US009939644B2

(12) United States Patent
Moran et al.

(10) Patent No.: US 9,939,644 B2
(45) Date of Patent: Apr. 10, 2018

(54) TECHNOLOGIES FOR CONTROLLING VISION CORRECTION OF A WEARABLE COMPUTING DEVICE

(71) Applicant: Intel Corporation, Santa Clara, CA (US)

(72) Inventors: Michael T. Moran, Naas (IE); Casey Baron, Chandler, AZ (US); Tobias M. Kohlenberg, Portland, OR (US); Stephen C. Chadwick, Chandler, AZ (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 14/750,923

(22) Filed: Jun. 25, 2015

(65) Prior Publication Data

US 2016/0377864 A1 Dec. 29, 2016

(51) Int. Cl.
*G02B 27/01* (2006.01)
*G06F 1/16* (2006.01)
(Continued)

(52) U.S. Cl.
CPC ..... *G02B 27/0172* (2013.01); *G02B 27/0189* (2013.01); *G06F 1/163* (2013.01);
(Continued)

(58) Field of Classification Search
CPC .. G02B 27/0172; G02B 27/0189; G02C 7/10; G06T 15/00
(Continued)

(56) References Cited

U.S. PATENT DOCUMENTS

2008/0151175 A1* 6/2008 Gross .................... G02C 7/086
351/45
2013/0106674 A1 5/2013 Wheeler
(Continued)

FOREIGN PATENT DOCUMENTS

WO 2013-067230 5/2013

OTHER PUBLICATIONS

International Search Report for PCT/US16/034115, dated Aug. 26, 2016 (3 pages).
Written Opinion for PCT/US16/034115, dated Aug. 26, 2016 (9 pages).

*Primary Examiner* — Tony Davis
(74) *Attorney, Agent, or Firm* — Barnes & Thornburg LLP

(57) ABSTRACT

Technologies for controlling vision correction of a wearable computing device includes controlling an opacity of an adjustable lens of the wearable computing device to generate a viewing port through the adjustable lens such that a region defined by the viewing port has an opacity less than a remaining region of the adjustable lens. For example, the opacity of the adjustable lens may be increased except for the region defined by the viewing port. In use, the wearable computing device may adjust the location, size, and/or shape of the viewing port based on a predefined prescription, the direction of the user's gaze, the user's viewing context, and/or other criteria. Additionally or alternatively, an image may be displayed on an external display surface of the adjustable lens. The wearable computing device may include multiple adjustable lens, each of which may be controlled in a similar manner.

25 Claims, 8 Drawing Sheets

(51) Int. Cl.
  *G06F 3/14* (2006.01)
  *G06F 3/01* (2006.01)
  *G06F 3/147* (2006.01)
  *G09G 5/14* (2006.01)

(52) U.S. Cl.
  CPC .............. *G06F 3/011* (2013.01); *G06F 3/013* (2013.01); *G06F 3/14* (2013.01); *G06F 3/147* (2013.01); *G09G 5/14* (2013.01); *G02B 2027/014* (2013.01); *G02B 2027/0138* (2013.01); *G02B 2027/0178* (2013.01)

(58) Field of Classification Search
  USPC .................. 345/8, 419, 156, 633; 351/45
  See application file for complete search history.

(56) References Cited

U.S. PATENT DOCUMENTS

| | | | |
|---|---|---|---|
| 2013/0187943 A1 | 7/2013 | Bohn | |
| 2014/0043320 A1* | 2/2014 | Tosaya | G02B 27/0172 345/419 |
| 2014/0184775 A1 | 7/2014 | Drake et al. | |
| 2014/0320399 A1* | 10/2014 | Kim | G02B 27/0172 345/156 |
| 2014/0354688 A1* | 12/2014 | Min | G06T 19/006 345/633 |
| 2016/0216515 A1* | 7/2016 | Bouchier | G03H 1/0808 |
| 2016/0377864 A1* | 12/2016 | Moran | G02B 27/0172 345/8 |

* cited by examiner

TECHNOLOGIES FOR CONTROLLING VISION CORRECTION OF A WEARABLE COMPUTING DEVICE

BACKGROUND

Some people suffer from various eye disorders and/or diseases. One such eye disorder that can particularly affect young children is known as Amblyopia, sometimes informally referred to as "lazy eye." Amblyopia can cause decreased vision and/or control of the affected eye. Of course, other disorders can cause similar issues.

A common treatment for such eye disorders is the use of a patch to cover the good eye. The covering the good eye with an eye patch, the patent is forced to use their amblyopic or "bad" eye, which can result in improvement of the eye disorder over time. Unfortunately, the use of an eye patch can cause a social stigma, especially with young children, which can reduce the adherence by the patient to the prescribed treatment by the patient. Additionally, a typical eye patch has no ability to adjust behavior over time or provide any feedback regarding the patient's progress. Rather, a doctor visit is typically required to determine the progress of the treatment, resulting in loss time and inconvenience for the patient.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

Figure 1:
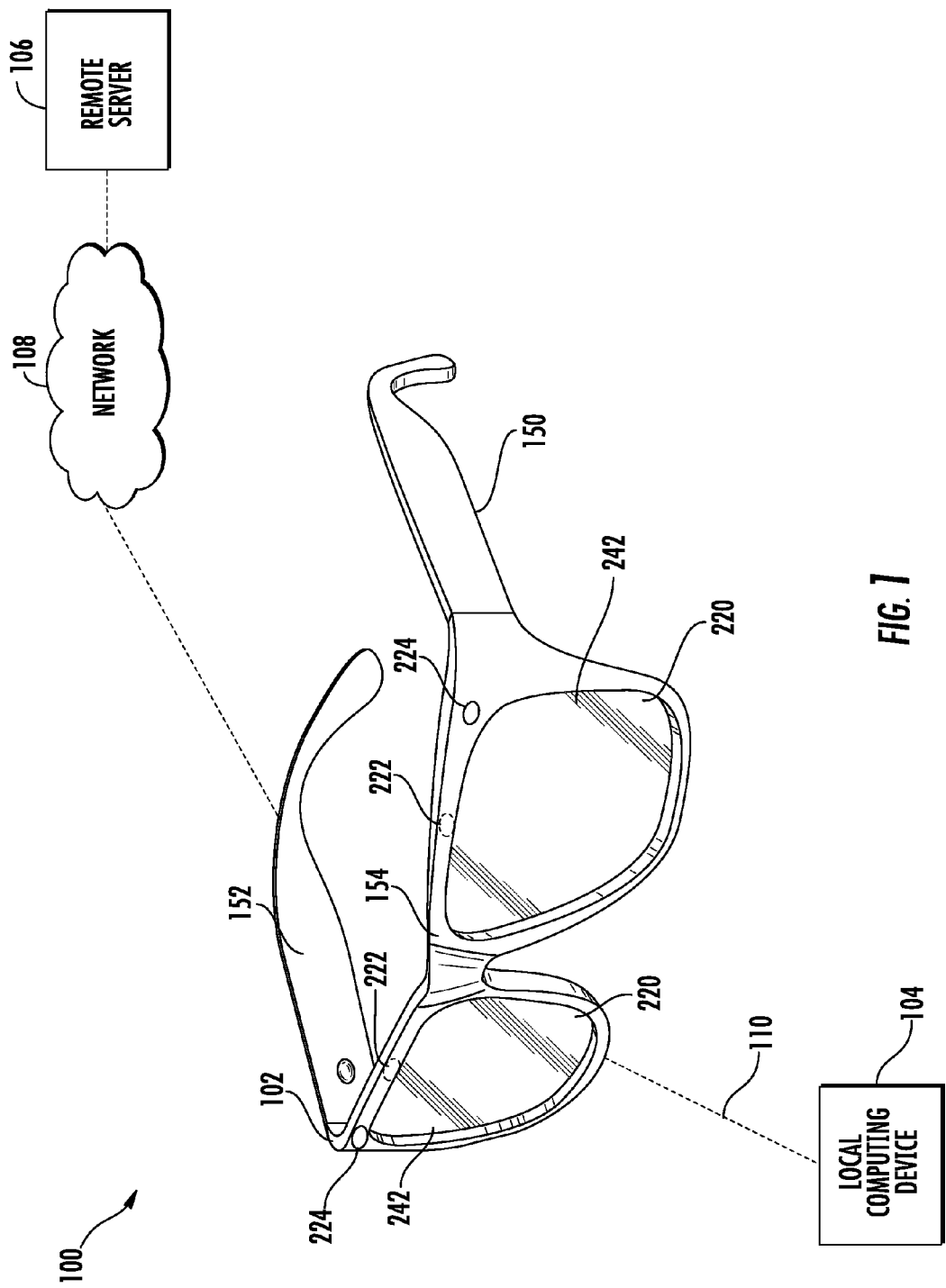
FIG. 1 is a simplified block diagram of at least one embodiment of a system for controlling vision correction of a wearable computing device.
Figure 2:
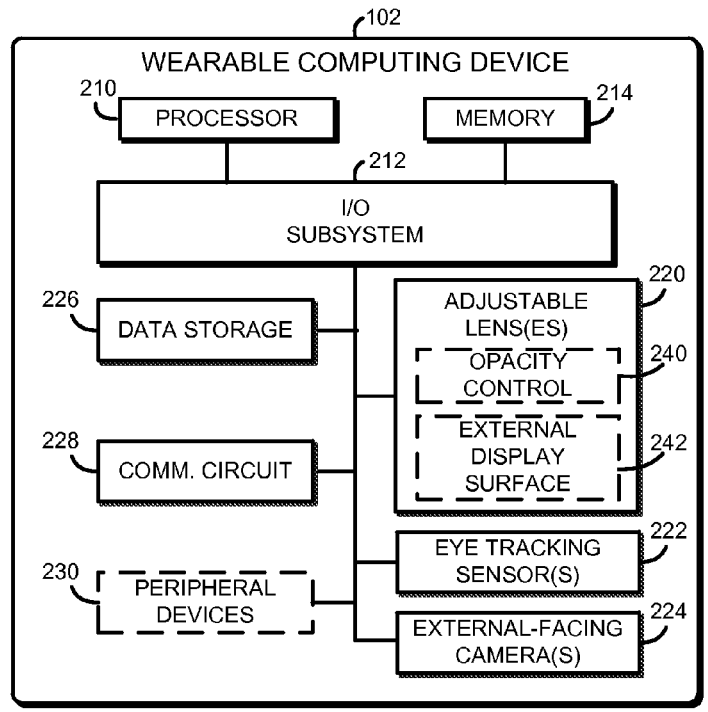
FIG. 2 is a simplified block diagram of at least one embodiment of a wearable computing device of the system of FIG. 1

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, a system 100 for controlling vision correction includes a wearable computing device 102, a local computing device 104, and a remote server 106, which may communicate with the wearable computing device 102 over a network 108. In use, the wearable computing device 102 is configured to control an adjustable lens 220 of the device 102 to provide an amount of vision correction to a user. To do so, as discussed in more detail below, wearable computing device 102 may control the opacity of the controlled adjustable lens 220 to generate a viewing port 900 (see, e.g., FIG. 9) through the otherwise opaque adjustable lens 220 for a corresponding eye of the user. By defining a viewing port 900 through the adjustable lens 220, the vision of the user may be focused, moved about, or otherwise controlled according to a prescription or pre-defined routine to provide an amount of correction to the user's eye over time. For example, by controlling the location, shape, and/or size of the viewing port 900, the wearable computing device 102 may step the user through a set of exercises designed to improve the operation of the user's eye. Such exercises and other prescription data may be received from the remote server 106 over the network 108. Additionally, the wearable computing device 102 may track the user's progress over time and transmit progress data to the remote server 106 for evaluation by a healthcare provider, who may adjust or modify the exercises and/or prescription based on the progress data. The remote server 106 may subsequently transmit any updated exercises/prescriptions back to the wearable computing device 102, which may update the control of the viewing port 900 based on the updated exercises and/or prescriptions.

In some embodiments, the wearable computing device 102 may also adaptively control the viewing port 900 over time based on various criteria. For example, in some embodiments, the wearable computing device 102 may be configured to determine a gaze direction of an eye of the user and control the viewing port 900 based on the determined gaze direction. In such embodiments, the wearable computing device 102 may adjust the location, size, and/or shape of the viewing port 900 based on the present gaze direction of the user. Similarly, the wearable computing device 102 may control the viewing port 900 based on a focus magnitude or focal point of the eye of the user. The gaze direction and focus magnitude of the user may be determined based on eye tracking sensor data generated by one or more eye tracking sensors 222 of the wearable computing device 102.

In some embodiments, the wearable computing device 102 may additionally or alternatively adaptively control the viewing port 900 based on a viewing context of the user. To do so, the wearable computing device 102 may determine a viewing context of the user based on an image generated by one or more external-facing cameras 224 and control the location, size, and/or shape of the viewing port 900 based on the determined viewing context. For example, if the wearable computing device 102 determines that the user is reading a book based on an analysis of the image generated by the external-facing cameras 224, the wearable computing device 102 may adjust the viewing port 900 to facilitate or correct up-close viewing.

Figure 8:
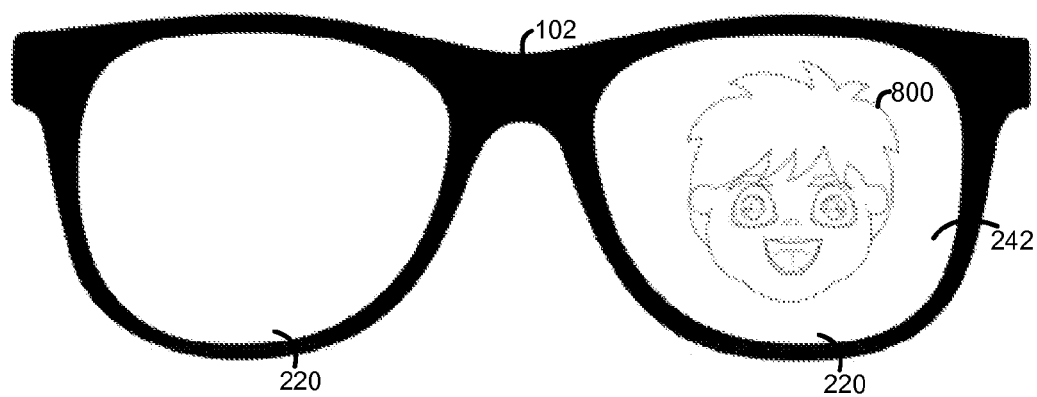
FIG. 8 is a simplified illustration of at least one embodiment of the wearable computing device of FIGS. 2 and 3 during execution of the method of FIG. 4.

Additionally, in some embodiments, the wearable computing device 102 may include one or more external display surfaces 242 on which an image may be displayed (see, e.g., FIG. 8). As discussed below, the image may be retrieved from a local data storage of the wearable computing device 102 or may be received from the local computing device 104 via a local communication link 110. The image may be embodied as any type of image, such as an image desirable to the user (e.g., a cartoon character for a child user). It should be appreciated that the stigma typically associated with vision correction treatments may be reduced by displaying a funny or interesting image on the external display surface 242, which may result in better user adherence to a prescribed routine and/or exercise.

Figure 3:
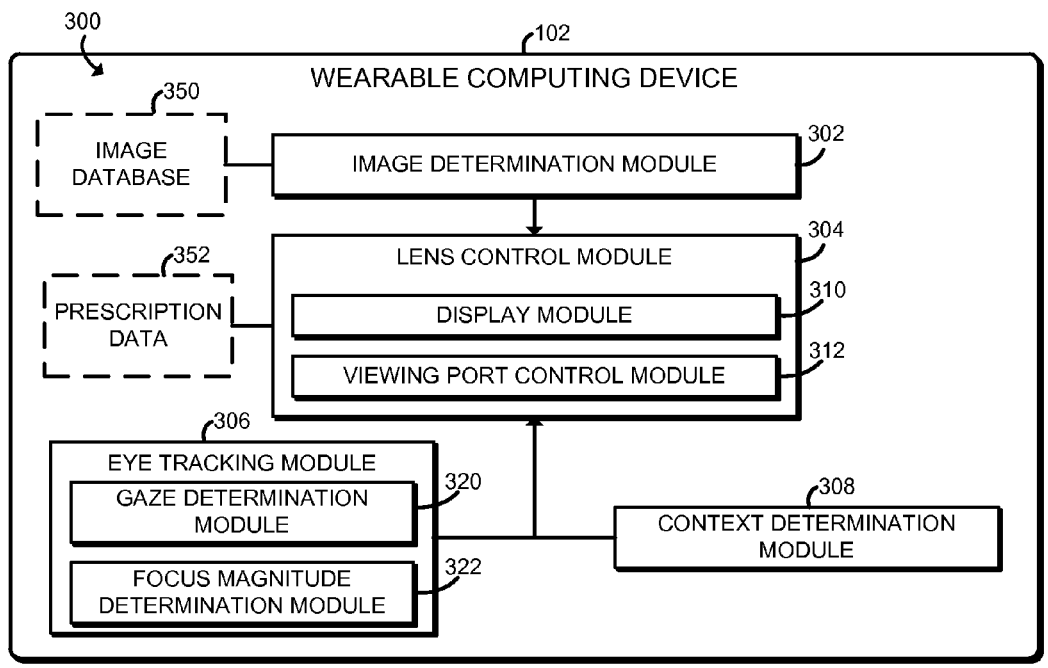
FIG. 3 is a simplified block diagram of at least one embodiment of an environment that may be established by the wearable computing device of FIG. 2.

The wearable computing device 102 may be embodied as any type of computing device capable of controlling vision correction and otherwise performing the functions described herein. For example, the wearable computing device 102 may be embodied as or include, without limitation, smart eyeglasses, a smart eyepatch, a head-mounted display, a smart cap or hat, a head-worn computer, or any other computing device capable of controlling vision correction of the user. As shown in FIG. 3, the illustrative wearable computing device 102 includes a processor 210, an I/O subsystem 212, a memory 214, one or more adjustable lens 220, one or more eye tracking sensors 222, one or more external-facing cameras 224, a data storage 226, and a communication circuit 228. Of course, the wearable computing device 102 may include other or additional components, such as those commonly found in a computer (e.g., various input/output devices), in other embodiments. Additionally, in some embodiments, one or more of the illustrative components may be incorporated in, or otherwise form a portion of, another component. For example, the memory 214, or portions thereof, may be incorporated in the processor 210 in some embodiments.

Some or all of the components of the wearable computing device 102 may be positioned close to the user's eyes. For example, as shown in FIG. 1, the adjustable lens 220 may be supported by an eyeglasses frame 150 configured to be worn on the user's face. Each of the eye tracking sensors 222 may be mounted to the eyeglasses frame 150 on an inner side 152 to facilitate viewing and tracking of the eyes of the user. Additionally, each of the external-facing cameras 224 may be mounted to an outer side 154 of the eyeglasses frame 150 to facilitate viewing of the external environment of the wearable computing device 102 as discussed in more detail below. Other components of the system such as the processor 210, I/O subsystem 212, memory 214, and data storage 226 may be located in the eyeglasses frame 150 or contained in a wearable housing that is in wireless or wired communication with components mounted to the eyeglasses frame 150. In other embodiments, the wearable computing device 102 may be formed by coupling appropriate components to an existing wearable device. For example, the individual components of the wearable computing device 102 may be coupled to or implemented in a head-mounted wearable computing device designed for heads-up display of information (e.g., "smart glasses").

The processor 210 may be embodied as any type of processor capable of performing the functions described herein. For example, the processor 210 may be embodied as a single or multi-core processor(s), digital signal processor, microcontroller, or other processor or processing/controlling circuit. Similarly, the memory 214 may be embodied as any type of volatile or non-volatile memory or data storage capable of performing the functions described herein. In operation, the memory 214 may store various data and software used during operation of the wearable computing device 102 such as operating systems, applications, programs, libraries, and drivers. The memory 214 is communicatively coupled to the processor 210 via the I/O subsystem 212, which may be embodied as circuitry and/or components to facilitate input/output operations with the processor 210, the memory 214, and other components of the wearable computing device 102. For example, the I/O subsystem 212 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 212 may form a portion of a system-on-a-chip (SoC) and be incorporated, along with the processor 210, the memory 214, and other components of the wearable computing device 102, on a single integrated circuit chip.

The adjustable lens 220 may be embodied as any type of eyeglass lens having a controllable opacity. For example, in the illustrative embodiment, each adjustable lens 220 includes an electrically controllable opacity control 240, which is configured to adjust the opacity of the corresponding adjustable lens 220 based on one or more electrical signals. Additionally, the adjustable lens 220 allows locality-based control of the opacity of the adjustable lens 220, which facilitates the generation of a viewing port 900 through the adjustable lens 220. That is, the opacity of the regions of the adjustable lens 220 outside the defined viewing port 900 may be separately controlled such that those regions may have an opacity different than the viewing port 900 (e.g., the viewing port 900 may be transparent while the regions outside the viewing port 900 may be opaque.)

In some embodiments, each adjustable lens 220 may also include an external display surface 242. The external display surface 242 may be embodied as any type of display device that facilitates the displaying of an image on the adjustable lens 220 as discussed in more detail below. In some embodiments, the external display surface 242 may be opaque so as to render the corresponding adjustable lens 220 opaque when an image is displayed thereon. Alternatively, in other embodiments, the external display surface 242 may be transparent or substantially transparent so as to facilitate a viewing port 900 through the displayed image as needed.

The eye tracking sensor(s) 222 may be embodied as any one or more active or passive sensors capable of determining a direction in which the user's gaze is directed. For example, in some embodiments, the eye tracking sensor(s) 222 may use active infrared emitters and infrared detectors to track the viewer's eye movements over time. The eye tracking sensor(s) 222 may capture the infrared light reflected off of various internal and external features of the viewer's eye and thereby calculate the direction of the viewer's gaze. In other embodiments, the eye tracking sensor(s) 222 may be embodied as a video camera capable of recording the user's eye motion. In embodiments including multiple eye tracking sensors 222, the sensors 222 may gather eye tracking data for both of the user's eyes to improve tracking accuracy. Additionally, in some embodiments, the eye tracking sensor(s) 222 may facilitate the determination of a focus magnitude and/or focal point of the user eye(s). The focus magnitude is indicative of the amount of focus exhibited by the user's eye at that particular point in time. For example, the focus magnitude may be determined based on an image of the user's eye (e.g., based on the size of the iris of the user's eye). In other embodiments, the eye tracking sensor(s) 222 may perform three-dimensional eye tracking, which tracks both the gaze direction of the user's eye along with the distance at which the user's eye is focused. For example, the eye tracking sensor 222 may determine a viewing angle for both of the user's eyes, allowing the distance to the object to be calculated and an amount of focus magnitude to be determined based thereon.

The external-facing camera(s) 224 may be embodied as any type of digital camera or other digital imaging device capable of being mounted to the eyeglasses frame 150 of the wearable computing device 102 or otherwise communicatively coupled to the wearable computing device 102. The external-facing camera 224 may include an electronic image sensor, such as an active-pixel sensor (APS), e.g., a complementary metal-oxide-semiconductor (CMOS) sensor, or a charge-coupled device (CCD). The external-facing camera(s) 224 may be used to capture images of the external environment relative to the wearable computing device 102 including still and/or video images.

The data storage 226 may be embodied as any type of device or devices configured for the short-term or long-term storage of data. For example, the data storage 226 may include any one or more memory devices and circuits, memory cards, hard disk drives, solid-state drives, or other data storage devices. The data storage 226 may store various data used by the wearable computing device 102 during operation. For example, in some embodiments, the data storage 226 may store a collection of images that may be displayed on the external display surface 242 of the adjustable lens 220. Additionally, in some embodiments, the data storage 226 may store prescription data, which may define eye exercises to be performed by the user based on control of the viewing port 900 as discussed below.

The communication circuit 228 may be embodied as any communication circuit, device, or collection thereof, capable of enabling communications between the wearable computing device 102 and the local computing device 104 over the communication link 110 and the remote server 106 via the network 108. To do so, the communication circuit 228 may be configured to use any one or more communication technology and associated protocols (e.g., Ethernet, Bluetooth®, Wi-Fi®, WiMAX, etc.) to effect such communication.

In some embodiments, the wearable computing device 102 may also include one or more peripheral devices 230. The peripheral devices 230 may include any type of peripheral device commonly found in a wearable computer, such as various input/output devices. For example, the peripheral devices 230 may include display circuitry, various input buttons and switches, speaker, microphone, and/or other peripheral devices.

Referring back to FIG. 1, the local computing device 104 is configured to communicate with the wearable computing device 102 over the communication link 110 as discussed above. For example, a user of the local computing device 104 may upload images for display on the external display surfaces 242. The local computing device 104 may be embodied as any type of computing device capable of communicating with the wearable computing device 102 and performing the functions described herein. For example, the local computing device 104 may be embodied as a smartphone, a tablet computer, a laptop computer, a notebook, a desktop computer, a server, a distributed computing system, a multiprocessor system, a multi-computer system, and/or other computing device. As such, the local computing device 104 may include components commonly found in a computing device. For example, the local computing device 104 may include one or more processors, memory, I/O subsystems, and communication circuits. Those components of the local computing device 104 may be similar to the corresponding components of the wearable computing device 102, the description of which is equally applicable to the components of the local computing device 104 and is not repeated herein for the clarity of description. It should be appreciated that although a single local computing device 104 is shown in FIG. 1, the system 100 may include additional local computing devices 104 in other embodiments.

The remote server 106 is also configured to communicate with the wearable computing device 102 over the network 108 as discussed above. For example, the remote server 106 may receive usage data from the wearable computing device, which may be indicative of the user's usage of the wearable computing device 102 over time. Additionally, the remote server 106 may transmit updated prescription data, which may define various exercises or control patterns for the adjustable lens 220 of the wearable computing device 102. The remote server 106 may be embodied as any type of computing device capable of communicating with the wearable computing device 102 and performing the functions described herein. For example, the remote server 106 may be embodied a server, a rack-mounted server, a blade server, a network appliance, a web appliance, a distributed computing system, a processor-based system, a mobile computing device, a smartphone, a tablet computer, a computer, a laptop computer, a desktop computer, multiprocessor system, and/or a consumer electronic device. As such, the remote server 106 may include components commonly found in a computing device. For example, the remote server 106 may include one or more processors, memory, I/O subsystems, and communication circuits. Those components of the remote server 106 may be similar to the corresponding components of the wearable computing device 102, the description of which is equally applicable to the components of the remote server 106 and is not repeated herein for the clarity of description. It should be appreciated that although a single remote server 106 is shown in FIG. 1, the system 100 may include additional remote servers 106 in other embodiments.

The network 108 may be embodied as any type of communication network capable of facilitating communication between the wearable computing device 102 and the remote server 106. As such, the network 108 may include one or more networks, routers, switches, computers, and/or other intervening devices. For example, the network 108 may be embodied as or otherwise include one or more local or wide area networks, cellular networks, publicly available global networks (e.g., the Internet), an ad hoc network, a short-range communication network or link, or any combination thereof.

Referring now to FIG. 3, in use, the wearable computing device 102 establishes an environment 300. The illustrative environment 300 includes an image determination module 302, a lens control module 304, an eye tracking module 306, and a context determination module 308. Each of the modules and other components of the environment 300 may be embodied as firmware, software, hardware, or a combination thereof. For example the various modules, logic, and other components of the environment 300 may form a portion of, or otherwise be established by, the processor 210, the I/O subsystem 212, an SoC, or other hardware components of the wearable computing device 102. As such, in some embodiments, any one or more of the modules of the environment 300 may be embodied as a circuit or collection of electrical devices (e.g., an image determination circuit, a lens control circuit, an eye tracking circuit, a context determination circuit, etc.).

In those embodiments in which the wearable computing device 102 is configured to display images on the external display surface 242 of the adjustable lens 220, the image determination module 302 is configured to determine the image to be displayed. To do so, the image determination module 302 may select the image randomly or based on a selection by the user. In some embodiments, the image determination module 302 may retrieve the image from an image database 350, which may be stored in the data storage 226 of the wearable computing device 102. In other embodiments, the image determination module 302 may receive the image to be displayed from the local computing device 104 via the communication link 110. In still other embodiments, a user of the local computing device 104 may interact with the image determination module 302 to select one or more images from the image database 350 for display on the external display surface 242. Additionally, in some embodiments, a user may define a display rotation of multiple images to be displayed by the wearable computing device 102.

The lens control module 304 is configured to control the operation of the adjustable lens 220. To do so, the lens control module 304 includes a display module 310 and a viewing port control module 312. The display module 310 is configured to control the display of an image on the external display surface 242 of the adjustable lens 220 in those embodiments facilitating displaying of images. As discussed above, the display module 310 may display a single, selected image or display a rotation of images based on user selection.

The viewing port control module 312 is configured to control the opacity control 240 of the adjustable lens 220 to generate the viewing port 900. For example, the viewing port control module 312 may control the location of the viewing port 900, as well as the size and/or shape of the viewing port 900. To do so, the viewing port control module 312 may be configured to adjust the opacity of the adjustable lens 220 to define the viewing port in the desired location and at the desired size and shape. For example, in embodiments in which the adjustable lens 220 is "normally transparent," the viewing port control module 312 may increase the opacity of the regions of the adjustable lens 220 outside of the region defined by the viewing port 900, while leaving the opacity of viewing port low so that the viewing port is substantially transparent. Alternatively, in embodiments in which the adjustable lens 220 is "normally opaque," the viewing port control module 312 may be configured to decrease the opacity of the viewing port 900, while leaving the remaining regions of the adjustable lens 220 opaque.

The viewing port control module 312 may be configured to adjust, modify, or otherwise control the viewing port 900 based on various criteria. For example, in some embodiments, the viewing port control module 312 may control the viewing port 900 based on prescription data 352, which may be stored in the data storage 226. As discussed above, the prescription data may define aspects of the viewing port 900, such as the size, shape, and/or location of the viewing port 900, and/or exercises to be performed by the user (e.g., by moving or modifying the viewing port 900 according to the exercise to be performed). Additionally or alternatively, in some embodiments, the viewing port control module 312 may adaptively control the viewing port 900 based on movement of the user's eyes as determined by the eye tracking module 306 and/or a viewing context of the user as determined by the context determination module 308.

The eye tracking module 306 is configured to generate eye tracking data indicative of the movement or gaze of the user's eye. To do so, the eye tracking module may include a gaze determination module 320 configured to determine a gaze direction of the user's eye based on the eye tracking sensor data generated by the eye tracking sensors 222. The gaze direction is indicative of the direction at which the user's corresponding eye is presently looking. Similarly, the focus magnitude determination module 322 is configured to determine an amount of focus of the user's corresponding eye based on the eye tracking sensor data generated by the eye tracking sensors 222. For example, the focus magnitude determination module 322 may determine the amount of focus based on the size of the iris of the corresponding eye.

It should be appreciated that the focus magnitude may be embodied as an absolute value or a relative value depending on the particular implementation. Regardless, the eye tracking module 306 is configured to provide the gaze direction data and the focus magnitude data to the lens control module 304, which may control the adjustable lens 220 (i.e., control the viewing port 900) based thereon.

The context determination module 308 is configured to determine a viewing context of the user based on one or more images generated by the external-facing camera(s) 224. To do so, the context determination module 308 may utilize any suitable image analysis algorithm to analyze the generated images and determine a context of the user's environment based thereon. For example, in some embodiments, the context determination module 308 may utilize an object detection or identification algorithm to identify objects in the captured images and determine a context of the user based on the identity of the objects. In some embodiments, the context determination module 308 may determine an activity being presently performed by the user. For example, the context determination module 308 may determine that the user is presently reading a book based on identifying a book from the images generated by the external-facing camera(s) 224. The context determination module 308 is configured to provide context data indicative of the user's viewing context to the lens control module 304, which may control the adjustable lens 220 (i.e., control the viewing port 900) based thereon.

Figure 4:
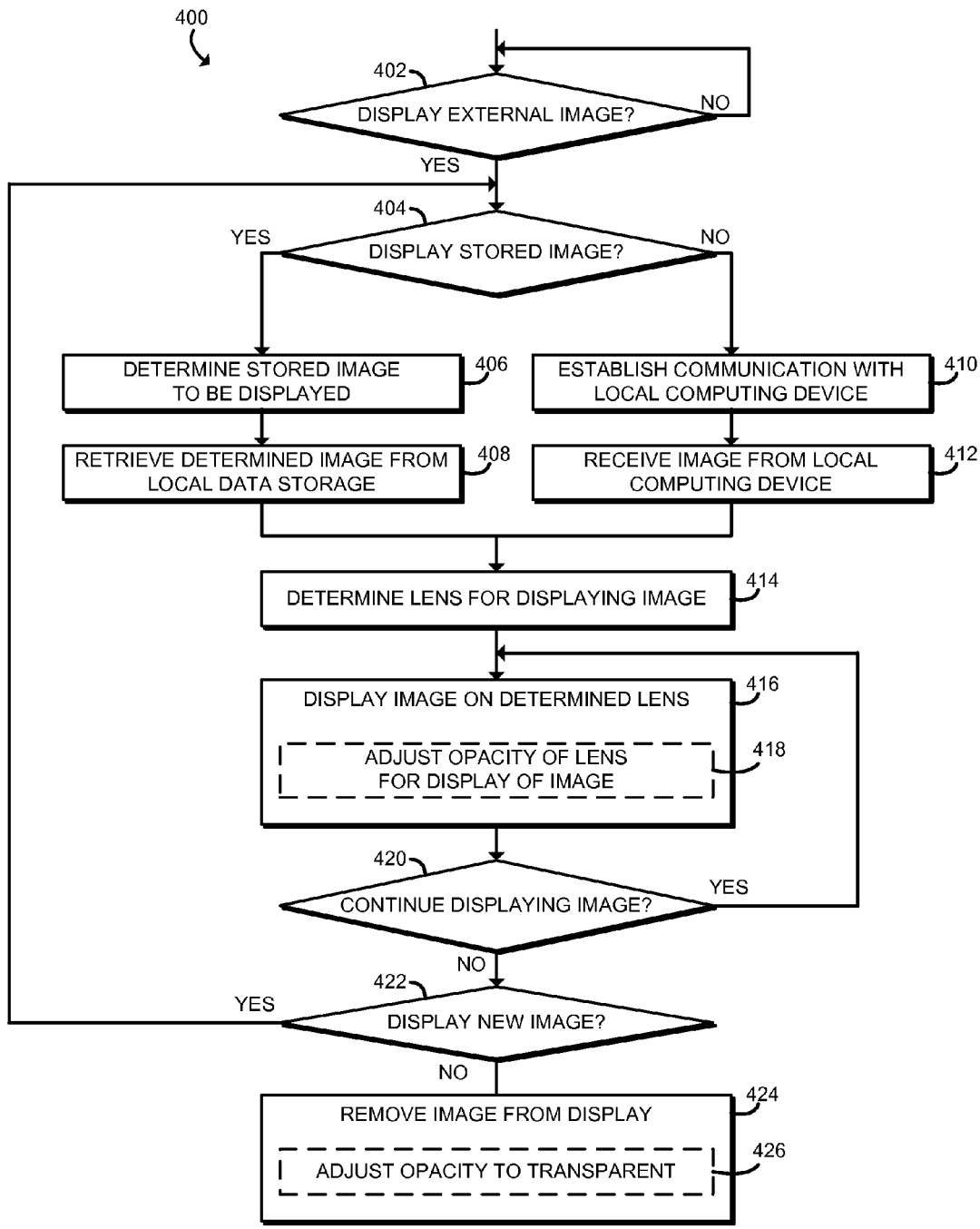
FIG. 4 is a simplified flow diagram of at least one embodiment of a method for displaying an image on an external display of an adjustable lens, which may be executed by the wearable computing device of FIGS. 2 and 3.

Referring now to FIG. 4, in use, the wearable computing device 102 may execute a method 400 for displaying an image on an external display surface 242 of an adjustable lens 220. The method 400 begins with block 402 in which the wearable computing device 102 determines whether to display an external image. As discussed above, the wearable computing device 102 may display an image on an external display surface 242 of an adjustable lens 220 as a stand-alone treatment or in conjunction with the use of a viewing port 900 as discussed below in regard to FIGS. 5-7. Regardless, if the wearable computing device 102 determines that an image is to be displayed on an adjustable lens 220, the method 400 advances to block 404 in which the wearable computing device 102 determines whether the image to be displayed is stored locally in the data storage 226 or is to be received from the local computing device 104. If the image to be displayed is already stored in the local data storage 226, the method 400 advances to block 406 in which the wearable computing device 102 determines which stored image to display. In some embodiments, the user of the wearable computing device 102 may select the image to be displayed (e.g., via actuation of suitable input devices of the wearable computing device 102). In other embodiments, a user of the local computing device 104 may communicate with the wearable computing device 102 to select the stored image for display. Additionally or alternatively, the wearable computing device 102 may randomly select the image to be displayed from those images stored in the data storage 226 or select the image based on some selection algorithm (e.g., based on recently selected images, the freshness of the images, etc.). Regardless, in block 408, the wearable computing device 102 retrieves the selected or determined image from the local data storage 226. The method 400 subsequently advances to block 414, which is discussed below.

Referring back to block 404, if the wearable computing device 102 determines that the image to be displayed is to be received from the local computing device 104, the method 400 advances to block 410. In block 410, the wearable computing device 102 establishes a communication link 110 with the local computing device 104 and subsequently receives the image to be displayed from the local computing device 104 in block 412.

After the image to be displayed on the external display surface 242 of the adjustable lens 220 has been retrieved from the local data storage 226 in block 408 or has been received from the local computing device 104 in block 412, the method 400 advances to block 414. In block 414, in embodiments in which the wearable computing device 102 includes multiple adjustable lenses 220, the wearable computing device 102 determines which adjustable lens 220 is to display the image. The selection of the adjustable lens 220 on which to display the image may be based on the prescription data 352 (e.g., based on the identity of the "bad eye" and/or the "good eye") or other criteria. For example, in some embodiments, the image may be displayed on the adjustable lens 220 corresponding to the "good eye" of the user. In such embodiments, the other adjustable lens 220 may control a viewing port 900 to train the "bad eye" of the user (see, e.g., the method 500 of FIG. 5). Of course, the selection of the adjustable lens 220 may be switched or modified as needed.

Once the desired adjustable lens 220 has been determined in block 414, the method 400 advances to block 416 in which the image is displayed on the external display surface 242 of the selected adjustable lens 220. The displayed image may be embodied as any type of image capable of being displayed on the external display surface 242. For example, in the illustrative embodiment of FIG. 8, a cartoon character image 800 is displayed on the external display surface 242 of the user's left adjustable lens 220. In some embodiments, the external display surface 242 may be substantially opaque, and the image may be displayed on the external display surface 242 without adjustment of the opacity of the adjustable lens 220. In other embodiments, the external display surface 242 may not be opaque, and the opacity of the adjustable lens 220 may be adjusted in block 418 to facilitate the display of the image on the external display surface 242. For example, the opacity of the adjustable lens 220 may be increased to better display the image on the external display surface 242.

After the image has been displayed on the external display surface 242 of the adjustable lens 220, the method 400 advances to block 420. In block 420, the wearable computing device 102 determines whether to continue displaying the image. For example, the wearable computing device 102 may be configured to display the image for a set period of time or until some reference event occurs (e.g., the powering down of the wearable computing device 102). If so, the method 400 loops back to block 416 in which the wearable computing device 102 continues to display the image. However, if the wearable computing device 102 determines not to continue display of the image, the method 400 advances to block 422. In block 422, the wearable computing device 102 determines whether to display a new image on the external display surface 242 of the adjustable lens 220. If so, the method 400 loops back to block 404 in which the wearable computing device 102 determines whether the new image is stored in the local data storage 226 or is to be received from the local computing device 104.

Referring back to block 422, if the wearable computing device 102 determines that no new image is to be displayed, the method 400 advances to block 424 in which the image is removed from the external display surface 242 of the adjustable lens 220. Additionally, in some embodiments, the wearable computing device adjusts the opacity of the adjustable lens 220 back to a reference setting, such as transparent or opaque setting.

Figure 5:
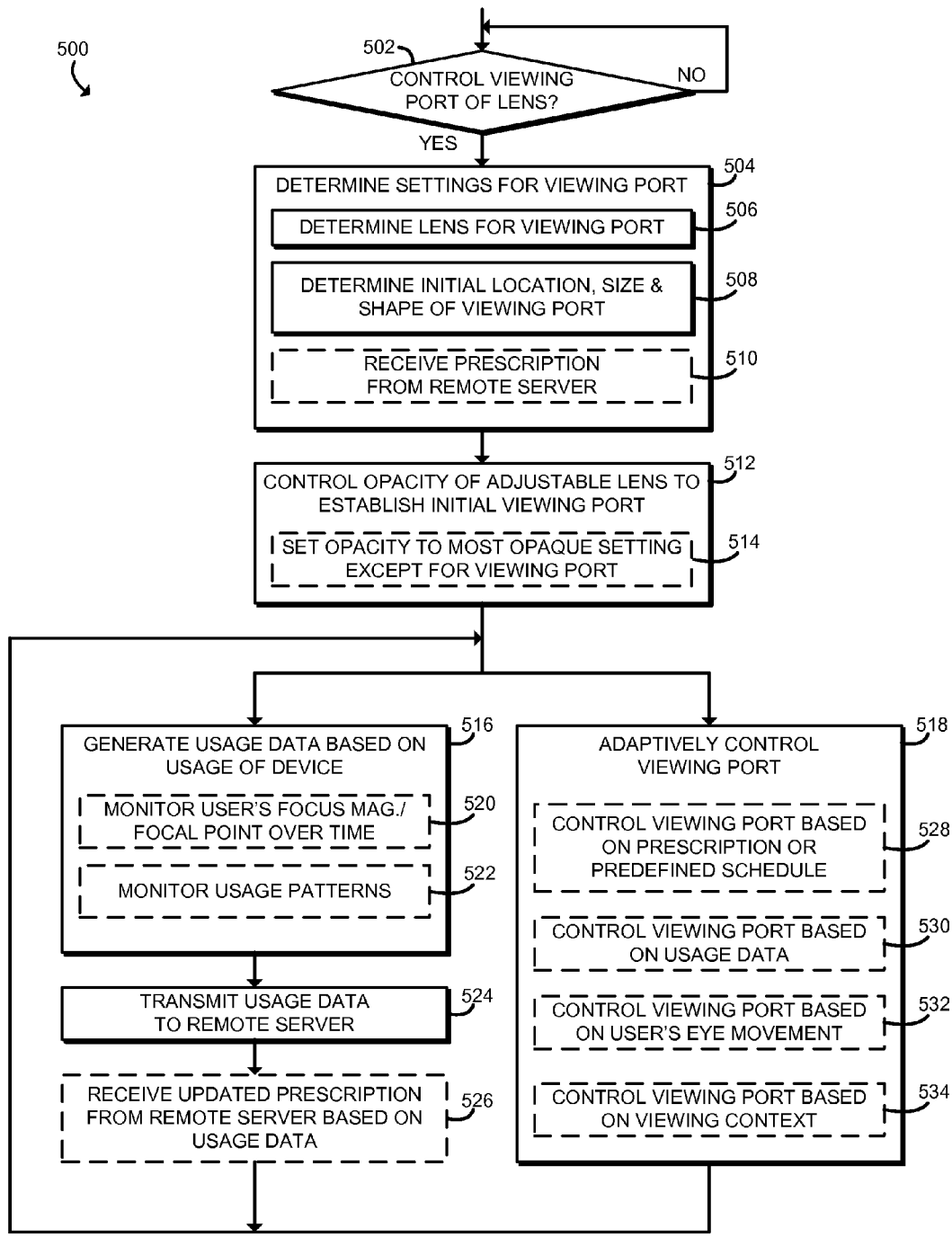
FIG. 5 is a simplified flow diagram of at least one embodiment of a method for adaptively controlling a viewing port of an adjustable lens, which may be executed by the wearable computing device of FIGS. 2 and 3.

Referring now to FIG. 5, in use, the wearable computing device 102 may also execute a method 500 for adaptively controlling an adjustable lens 220. The method 500 begins with block 502 in which the wearable computing device 102 determines whether to control a viewing port 900 of the adjustable lens 220. If so, the method 500 advances to block 504 in which the wearable computing device 102 determines initial settings for the viewing port 900. For example, in block 506, the wearable computing device 102 may determine which adjustable lens 220 is to have the viewing port 900. As discussed above, the selection of which adjustable lens 220 is to have the viewing port 900 may be based on the prescription data 352 (e.g., based on the identity of the "bad eye" and/or the "good eye") or other criteria. For example, in some embodiments, viewing port 900 is generated on the adjustable lens 220 corresponding to the "bad eye" of the user to facilitate training and treatment of the eye.

In block 508, the wearable computing device 102 determines an initial location, size, and/or shape of the viewing port 900. The initial location, size, and/or shape of the viewing port 900 may be defined by a reference or predefined settings, set by a user of the wearable computing device 102 (e.g., via actuation of suitable input devices of the wearable computing device 102), and/or determined based on the prescription data 352 stored in the data storage or received from the remote server 106 in block 510.

Figure 9:
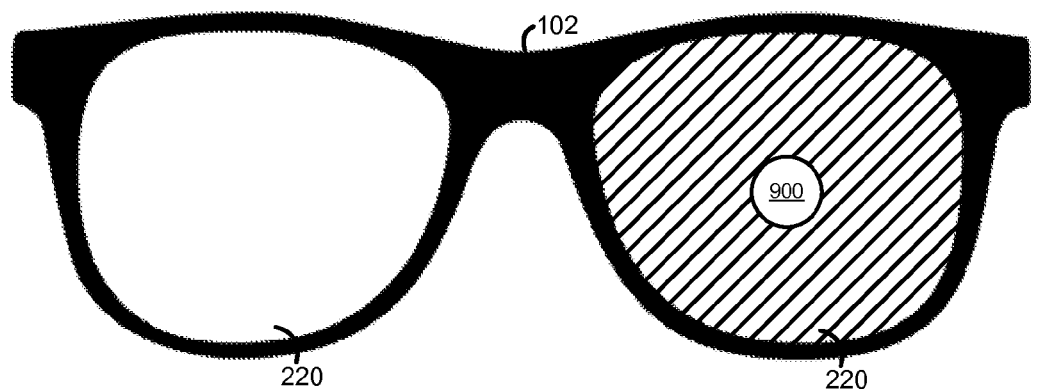
FIGS. 9-11 are simplified illustrations of various embodiments of the wearable computing device of FIGS. 2 and 3 during execution of the methods of FIGS. 5-7.

After the initial settings of the viewing port 900 have been determined in block 504, the wearable computing device 102 controls the opacity of the corresponding adjustable lens 220 to define the viewing port 900 in block 512. To do so, the wearable computing device 102 may control the opacity control 240 to adjust the opacity of the adjustable lens 220 as needed. For example, in some embodiments in block 514, the wearable computing device 102 may set the opacity of the adjustable lens 220 to the most opaque setting, except for that region defining the viewing port 900. That is, as shown in FIG. 9, the viewing port 900 may be established in the corresponding adjustable lens 220 by increasing the opacity of the region of the adjustable lens 220 outside the viewing port 900 or by decreasing the opacity of the region defining the viewing port 900, depending on the particular implementation. In the illustrative embodiment of FIG. 9, the viewing port 900 has an circular shape, but may have other shapes and sizes and be located in other locations, in other embodiments. Additionally, although the illustrative embodiment of FIG. 9 shows the viewing port 900 established in the user's left adjustable lens 220, the viewing port 900 may be established in the user's right adjustable lens 220 in other embodiments as discussed above.

After the viewing port 900 has been established in the corresponding adjustable lens 220, the method 500 advances to block 516 and 518, which may be executed in parallel with each other as shown in FIG. 5 or sequentially in other embodiments. In block 516, the wearable computing device 102 generates usage data based on the user's usage of the wearable computing device 102. For example, the wearable computing device 102 may monitor the user's focus magnitude or focal point over time. Such monitoring may occur, for example, during prescribed exercises conducted by the wearable computing device 102 as discussed below. Additionally, in block 522, the wearable computing device 102 may monitor the user's usage patterns over time. For example, the wearable computing device 102 may determine the time at which, and/or duration for which, the user wore the wearable computing device 102, completed specific exercises, and/or other data indicative of the user's usage of the wearable computing device 102. It should be appreciated that such usage data may be indicative of a user's progress with a treatment. As such, in block 524, the wearable computing device transmits the usage data to the remote server 106. In some embodiments, the wearable computing device 102 may receive an updated prescription, exercise, or other data that affects the operation of the wearable computing device 102 from the remote server 106 based on the usage data. For example, a healthcare provider may analyze the usage data and modify a previous prescription, set of exercises, or other operation of the wearable computing device 102 and transmit the updated prescription or other data to the wearable computing device 102 in block 526. Regardless, after the usage data has been transmitted to the remote server 106 in block 524 and/or the updated prescription or other data has been received in block 526, the method 500 loops back to blocks 516 and 518.

In block 518, the wearable computing device 102 adaptively controls the viewing port 900. To do so, the wearable computing device 102 may control any aspect of the viewing port 900 including, but not limited to, the location on the adjustable lens 220 of the viewing port 900, the size of the viewing port 900, and/or the shape of the viewing port 900. Additionally, the wearable computing device 102 may control the viewing port 900 based on any suitable criteria. For example, in some embodiments in block 528, the wearable computing device 102 may control the viewing port 900 based on the prescription data stored in the local data storage 226, the updated prescription data received in block 526, and/or according to another predefined schedule. That is, the wearable computing device 102 may adjust or modify any aspect of the viewing port 900 based on the prescription data which may, for example, define a set of exercises to be completed by the user of the wearable computing device 102 (e.g., an exercise requiring the user to visually follow the viewing port 900 as it is moved about). Additionally or alternatively, in some embodiments in block 530, the wearable computing device 102 may control the viewing port 900 based on the usage data as determined in block 516. That is, the wearable computing device 102 may be adjust or modify any aspect of the viewing port based on how the user is presently using the wearable computing device 102 (e.g., based on the length of use, periodicity of user, etc.)

Figure 6:
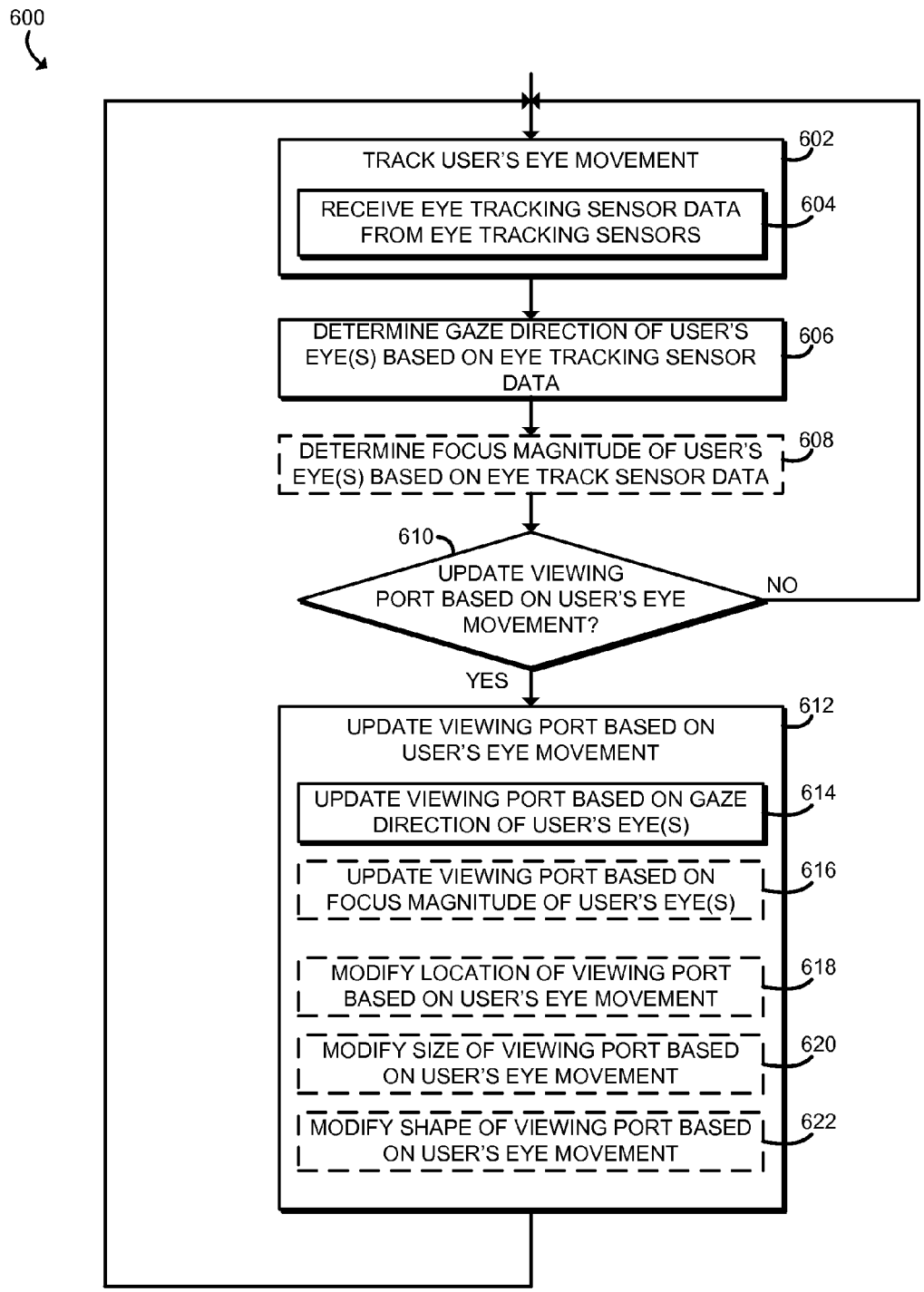
FIG. 6 is a simplified flow diagram of at least one embodiment of a method for controlling a viewing port of an adjustable lens based on the user's eye movement, which may be executed by the wearable computing device of FIGS. 2 and 3.

In some embodiments, in block 532, the wearable computing device 102 may additionally or alternatively control the viewing port 900 based on the user's eye movement. To do so, the wearable computing device 102 may execute a method 600 as shown in FIG. 6. The method 600 begins with block 602 in which the wearable computing device 102 tracks the movement of the user's corresponding eye. To do so, the wearable computing device 102 may receive eye tracking sensor data from the eye tracking sensors 222. In block 606, the wearable computing device 102 determines a gaze direction of the user's corresponding eye based on the eye tracking sensor data. That is, the wearable computing device 102 determines where the user's corresponding eye is presently looking. The direction of the user's gaze may be described using any convenient coordinate system or representation method. For example, the gaze direction may be embodied as an azimuth angle and a polar angle in a spherical coordinate system (i.e., $(\theta, \varphi)$). As another example, the gaze direction may be embodied as two-dimensional coordinates corresponding to the gaze direction projected on a reference plane. Additionally, the gaze direction may be determined after the eye tracking sensor data is filtered by the eye tracking sensor 222 or the wearable computing device 102 to eliminate high-frequency eye movements. Because human eye movement is characterized by short pauses, called fixations, linked by rapid movements, called saccades, the accuracy and/or usability of the wearable computing device 102 may be improved through such filtering.

In some embodiments, the wearable computing device 102 may also determine a focus magnitude or focal point of the corresponding user's eye based on the eye tracking sensor data in block 608. As discussed above, the focus magnitude may be indicative of the amount of focus of the user's eye at a particular point in time and may be determined, for example, based on the size of the iris of the user's eye. Alternatively, in other embodiments such as those in which the eye tracking sensors 222 are embodied as three-dimensional eye tracking sensors 222, the focal point of the user's eye may be determined based on the three-dimensional eye tracking data. That is, as described above, the three-dimensional eye tracking data may include data indicative of the distance at which the user's eye is focused.

Subsequently, in block 610, the wearable computing device 102 determines whether to update or adjust the viewing port 900 based on the determined user's eye movement data (e.g., based on the user's gaze direction and/or focus magnitude). For example, in some embodiments, the wearable computing device 102 may apply a threshold to the eye movement data and only adjust the viewing port 900 in response to deviation outside such threshold. It should be appreciated that the use of a threshold in this manner may reduce unwanted adjustment of the viewing port 900 in response to minimal eye movement.

If the wearable computing device 102 determines not to update the viewing port 900, the method 600 loops back to block 602 in which the wearable computing device continues to track the user's eye movement. Alternatively, if the wearable computing device 102 determines that the viewing port 900 should be updated or modified, the method 600 advances to block 612. In block 612, the wearable computing device 102 updates the viewing port based on the user's eye movement. To do so, in block 614, the wearable computing device 102 may update or modify the viewing port 900 based on the gaze direction of the user's corresponding eye. For example, if the user looks in a different direction, the wearable computing device 102 may adjust the location of the viewing port 900 based on the new gaze direction of the user's corresponding eye. Additionally, in some embodiments in block 618, the wearable computing device 102 may update or modify the viewing port 900 based on the focus magnitude or focal point of the user's corresponding eye. For example, if the wearable computing device 102 determines that the user is focusing on a close object (e.g., reading a book), the wearable computing device 102 may decrease the size of the viewing port 900 to help the user's corresponding eye focus on the nearby object.

Figure 10:
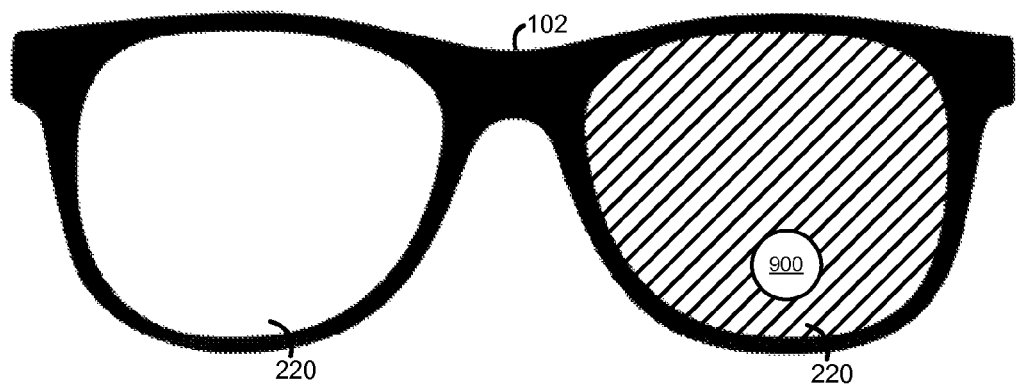
Figure 11:
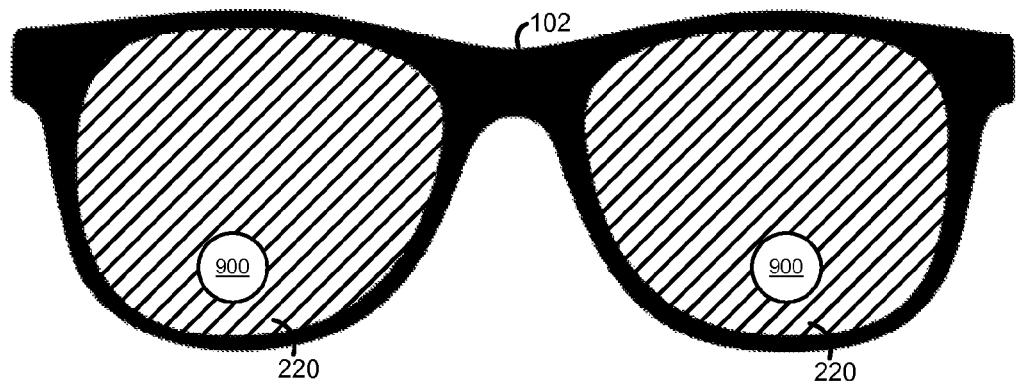

It should be appreciated that the wearable computing device 102 may update or modify any aspect of the viewing port 900 in block 612. For example, the wearable computing device 102 may update or modify the location of the viewing port 900 in block 618, the size of the viewing port 900 in block 620, and/or the shape of the viewing port 900 in block 622. In the illustrative embodiment of FIG. 10, for example, the wearable computing device 102 has updated the location of the viewing port 900 relative to the initial location shown in FIG. 9. Additionally, as discussed above, the wearable computing device 102 may establish and control a viewing port 900 in either adjustable lens 220 or in both adjustable lenses 220 as shown in FIG. 11. In such embodiments, the viewing ports 900 of the adjustable lens 220 may be controlled synchronously or asynchronously depending on the eye disorder of the user and/or the intended user of the wearable computing device 102. Regardless, after the wearable computing device 102 has updated the viewing port in block 612 of FIG. 6, the method 600 loops back to block 602 in which the wearable computing device 102 continues to track the user's eye movement.

Figure 7:
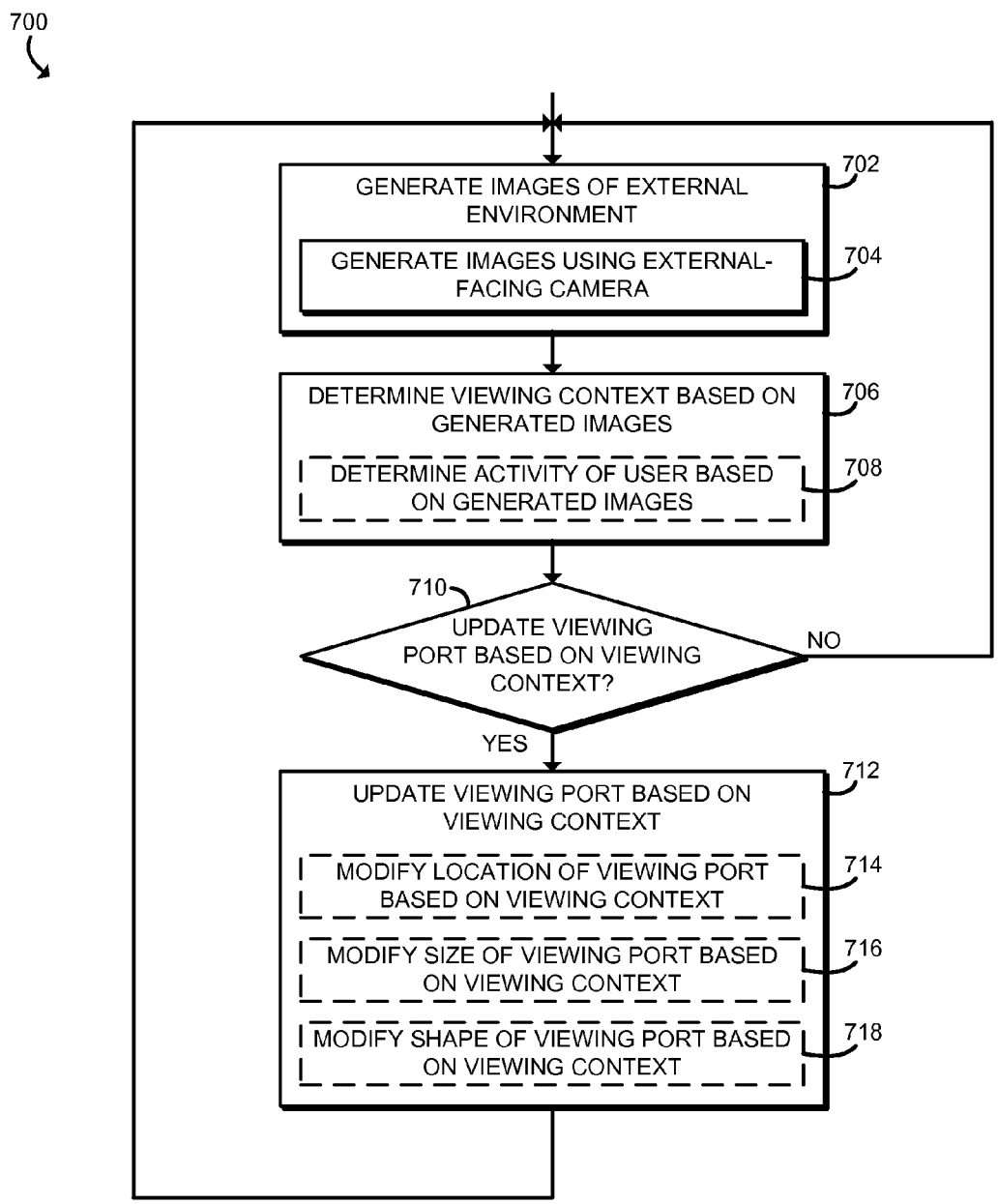
FIG. 7 is a simplified flow diagram of at least one embodiment of a method for controlling a viewing port of an adjustable lens based on a user's viewing context, which may be executed by the wearable computing device of FIGS. 2 and 3.

Referring back to FIG. 5, in some embodiments, the wearable computing device 102 may additionally or alternatively control the viewing port 900 based on a viewing context of the user in block 534. To do so, the wearable computing device 102 may execute a method 700 as shown in FIG. 7. The method 700 begins with block 702 in which the wearable computing device 102 generates images of the local external environment. To do so, the wearable computing device 102 may control the external-facing cameras 224 to generate the images in block 704. The images of the local external environment may be embodied as any type of image and/or collection of images (e.g., video). For example, in some embodiments, the images generated by the external-facing cameras 224 maybe embodied as three-dimensional images and may include associated depth data.

Subsequently, in block 706, the wearable computing device 102 may determine a viewing context of the user based on the images generated or captured in block 702. To do so, the wearable computing device 102 may utilize any suitable image analysis algorithm or technique. For example, in some embodiments, the wearable computing device 102 may utilize an object detection or identification algorithm to identify objects in the generated images and determined a context of the user based on the identity of the objects. In some embodiments, the wearable computing device 102 may determine an activity in which the user is presently engaged based on the generated images in block 708. For example, if the wearable computing device 102 determines that the user is presently looking at a book, the wearable computing device 102 may determine that the user is reading in block 708.

In block 710, the wearable computing device 102 determines whether to update or adjust the viewing port 900 based on the viewing context of the user. For example, the wearable computing device 102 may be configured to adjust or modify the viewing port 900 only in response to identifying specific pre-defined viewing contexts (e.g., the user is driving a car, the user is reading a book, etc.). If the wearable computing device 102 determines not to update the viewing port 900, the method 700 loops back to block 702 in which the wearable computing device 102 continues to generate images of the external environment. If, however, the wearable computing device 102 determines that the viewing port 900 should be updated, the method 700 advances to block 712 in which the wearable computing device 102 updates or modifies the viewing port 900 based on the determined viewing context of the user. The wearable computing device 102 may update or modify any aspect of the viewing port 900 in block 712. For example, the wearable computing device 102 may update or modify the location of the viewing port 900 in block 714, the size of the viewing port 900 in block 716, and/or the shape of the viewing port 900 in block 718. Regardless, after the viewing port 900 has been updated or modified in block 712, the method 700 loops back to block 702 in which the wearable computing device 102 continues to generate images of the external environment.

EXAMPLES

Illustrative examples of the technologies disclosed herein are provided below. An embodiment of the technologies may include any one or more, and any combination of, the examples described below.

Example 1 includes a wearable computing device to control vision correction, the wearable computing device comprising one or more adjustable lens, wherein each adjustable lens has an opacity that is electronically adjustable; one or more eye tracking sensors to generate eye tracking sensor data of an eye of a user; an eye tracking module to determine a gaze direction of the eye of the user based on the eye tracking data; and a lens control module to (i) control an opacity of an adjustable lens of the one or more adjustable lens to generate a viewing port through the adjustable lens and (ii) adjust the viewing port based on the gaze direction of the eye of the user, wherein a region defined by the viewing port has an opacity less than a remaining region of the adjustable lens.

Example 2 includes the subject matter of Example 1, and wherein the lens control module is to control the opacity of the adjustable lens to generate the viewing port based on a prescription received from a remote server.

Example 3 includes the subject matter of any of Examples 1 and 2, and wherein to control the opacity of the adjustable lens comprises to determine at least one of an initial location, initial size, or initial shape of the viewing port, and control the opacity of the adjustable lens to generate a viewing port at the initial location, having the initial size, or having the initial shape.

Example 4 includes the subject matter of any of Examples 1-3, and wherein the one or more eye tracking sensors are to generate tracking sensor data indicative of a gaze direction of each of two eyes of the user.

Example 5 includes the subject matter of any of Examples 1-4, and wherein to adjust the viewing port comprises to adjust the viewing port based on an elapsed time.

Example 6 includes the subject matter of any of Examples 1-5, and wherein to adjust the viewing port comprises to adjust at least one of a location, a size, or a shape of the viewing port.

Example 7 includes the subject matter of any of Examples 1-6, and wherein the eye tracking module is further to determine a focus magnitude of the eye of the user based on the eye tracking data, wherein the focus magnitude is indicative of an amount of focus exhibited by the eye of the user, and the lens control module is to adjust the viewing port based on the gaze direction and the focus magnitude of the user.

Example 8 includes the subject matter of any of Examples 1-7, and further including a camera to generate an image of an external environment of the wearable computing device; and a context determination module to determine a viewing context of the user based on the image of the external environment, wherein to adjust the viewing port comprises to adjust the viewing port based on the gaze direction of the user and the viewing context of the user.

Example 9 includes the subject matter of any of Examples 1-8, and wherein to determine a viewing context of the user comprises to determine a present activity performed by the user.

Example 10 includes the subject matter of any of Examples 1-9, and wherein the eye tracking module is further to generate usage data indicative of the user's usage of the wearable computing device over a period of time.

Example 11 includes the subject matter of any of Examples 1-10, and wherein to generate the usage data comprises to generate gaze data indicative of the gaze direction of the eye of the user over the period of time.

Example 12 includes the subject matter of any of Examples 1-11, and wherein to generate the usage data comprises to determine, a focus magnitude of the eye the user based on the eye tracking data, wherein the focus magnitude is indicative of an amount of focus exhibited by the eye of the user; and generate focus data indicative of the focus magnitude of the eye of the user over the period of time.

Example 13 includes the subject matter of any of Examples 1-12, and wherein the lens control module is further to transmit the usage data to a remote server and receive, from the remote server, and updated prescription based on to the usage data, wherein to adjust the viewing port comprises to adjust the viewing port based on the updated prescription.

Example 14 includes the subject matter of any of Examples 1-13, and wherein to adjust the viewing port comprises to adjust the viewing port based on the usage data.

Example 15 includes the subject matter of any of Examples 1-14, and wherein the lens control module is further to display an image on an external display surface of the adjustable lens.

Example 16 includes the subject matter of any of Examples 1-15, and further including a data storage, wherein the image is stored in the data storage and the lens control module is further to retrieve the image from the data storage.

Example 17 includes the subject matter of any of Examples 1-16, and wherein the lens control module is to establish a communication link with a local computing device, and receive the image from the local computing device via the communication link.

Example 18 includes the subject matter of any of Examples 1-17, and wherein to display the image comprises display the image for a reference period of time.

Example 19 includes the subject matter of any of Examples 1-18, and wherein the lens control module is further to determine whether to display a new image on the external display surface of the adjustable lens; and display a different image on the external display surface of the adjustable lens in response to a determination to display a new image.

Example 20 includes the subject matter of any of Examples 1-19, and wherein to display the image comprises to display the image on the adjustable lens without the viewing port.

Example 21 includes a wearable computing device to control vision correction, the wearable computing device comprising one or more adjustable lens, wherein each adjustable lens has an opacity that is electronically adjustable and includes an external display surface; an image determination module to determine an image for display on the external display surface of an adjustable lens of the one or more adjustable lens; and a lens control module to control the opacity of the adjustable lens and display the image on the external display surface of the adjustable lens.

Example 22 includes the subject matter of Example 21, and further including a data storage, wherein the image is stored in the data storage and the lens control module is further to retrieve the image from the data storage.

Example 23 includes the subject matter of any of Examples 21 and 22, and wherein the lens control module is to establish a communication link with a local computing device, and receive the image from the local computing device via the communication link.

Example 24 includes the subject matter of any of Examples 21-23, and wherein to display the image comprises display the image for a reference period of time.

Example 25 includes the subject matter of any of Examples 21-24, and wherein the lens control module is further to determine whether to display a new image on the external display surface of the adjustable lens; and display a different image on the external display surface of the adjustable lens in response to a determination to display a new image.

Example 26 includes a method for controlling vision correction of a wearable computing device, the method comprising controlling, by the wearable computing device, an opacity of an adjustable lens of the wearable computing device to generate a viewing port through the adjustable lens such that a region defined by the viewing port has an opacity less than a remaining region of the adjustable lens; receiving, by the wearable computing device, eye tracking sensor data from an eye tracking sensor of the wearable computing device; determining, by the wearable computing device, a gaze direction of an eye of a user of the wearable computing device based on the eye tracking sensor data; and adjusting, by the wearable computing device, the viewing port based on the gaze direction of the user.

Example 27 includes the subject matter of Example 26, and wherein controlling the opacity of the adjustable lens comprises controlling the opacity of the adjustable lens to generate a viewing port based on a prescription received from a remote server.

Example 28 includes the subject matter of any of Examples 26 and 27, and wherein controlling the opacity of the adjustable lens comprises determining at least one of an initial location, initial size, or initial shape of the viewing port, and controlling the opacity of the adjustable lens to generate a viewing port at the initial location, having the initial size, or having the initial shape.

Example 29 includes the subject matter of any of Examples 26-28, and wherein receiving the eye tracking sensor data comprises receiving eye tracking sensor data indicative of a gaze direction of each of two eyes of the user.

Example 30 includes the subject matter of any of Examples 26-29, and wherein adjusting the viewing port comprises adjusting, by the wearable computing device, the viewing port based on an elapsed time.

Example 31 includes the subject matter of any of Examples 26-30, and wherein adjusting the viewing port comprises adjusting at least one of a location, a size, or a shape of the viewing port.

Example 32 includes the subject matter of any of Examples 26-31, and further including determining, by the wearable computing device, a focus magnitude of the eye the user based on the eye tracking data, wherein the focus magnitude is indicative of an amount of focus exhibited by the eye of the user, and wherein adjusting the viewing port comprises adjusting, by the wearable computing device, the viewing port based on the gaze direction and focus magnitude of the user.

Example 33 includes the subject matter of any of Examples 26-32, and further including generating, by a camera of the wearable computing device, an image of an external environment of the wearable computing device; and determining, by the wearable computing device, a viewing context of the user based on the image of the external environment, wherein adjusting the viewing port comprises adjusting, by the wearable computing device, the viewing port based on the gaze direction of the user and the viewing context of the user.

Example 34 includes the subject matter of any of Examples 26-33, and wherein determining a viewing context of the user comprises determining an activity currently being performed by the user.

Example 35 includes the subject matter of any of Examples 26-34, and further including generating, by the wearable computing device, usage data indicative of the user's usage of the wearable computing device over a period of time.

Example 36 includes the subject matter of any of Examples 26-35, and wherein generating usage data comprises generating, by the wearable computing device, gaze data indicative of the gaze direction of the eye of the user over the period of time.

Example 37 includes the subject matter of any of Examples 26-36, and wherein generating the usage data comprises determining, by the wearable computing device, a focus magnitude of the eye the user based on the eye tracking data, wherein the focus magnitude is indicative of an amount of focus exhibited by the eye of the user; and generating, by the wearable computing device, focus data indicative of the focus magnitude of the eye of the user over the period of time.

Example 38 includes the subject matter of any of Examples 26-37, and further including transmitting, by the wearable computing device, the usage data to a remote server; and receiving, by the wearable computing device and from the remote server, an updated prescription based on the usage data, wherein adjusting the viewing port comprises adjusting, by the wearable computing device, the viewing port based on the updated prescription.

Example 39 includes the subject matter of any of Examples 26-38, and wherein adjusting the viewing port comprises adjusting, by the wearable computing device, the viewing port based on the usage data.

Example 40 includes the subject matter of any of Examples 26-39, and further including displaying an image on an external display surface of the adjustable lens.

Example 41 includes the subject matter of any of Examples 26-40, and further including retrieving, by the wearable computing device, the image from a local data storage of the wearable computing device.

Example 42 includes the subject matter of any of Examples 26-41, and further including establishing, by the wearable computing device, a communication link with a local computing device; and receiving, by the wearable computing device, the image from the local computing device via the communication link.

Example 43 includes the subject matter of any of Examples 26-42, and wherein displaying the image comprises displaying the image for a reference period of time.

Example 44 includes the subject matter of any of Examples 26-43, and further including determining, by the wearable computing device, whether to display a new image on the external display surface of the adjustable lens; and displaying, by the wearable computing device, a different image on the external display surface of the adjustable lens in response to a determination to display a new image.

Example 45 includes the subject matter of any of Examples 26-44, and wherein displaying the image comprises displaying the image on the adjustable lens without the viewing port.

Example 46 includes a method for controlling vision correction of a wearable computing device, the method comprising determining, by the wearable computing device, an image for display on an external display surface of an adjustable lens of the wearable computing device; and displaying, by the wearable computing device, the image on the external display surface of the lens of the wearable computing device, wherein displaying the image comprises electronically controlling an opacity of the adjustable lens.

Example 47 includes the subject matter of Example 46, and further comprising retrieving, by the wearable computing device, the image from a local data storage of the wearable computing device.

Example 48 includes the subject matter of any of Examples 46 and 47, and further including establishing, by the wearable computing device, a communication link with a local computing device; and receiving, by the wearable computing device, the image from the local computing device via the communication link.

Example 49 includes the subject matter of any of Examples 46-48, and wherein displaying the image comprises displaying the image for a reference period of time.

Example 50 includes the subject matter of any of Examples 46-49, and further including determining, by the wearable computing device, whether to display a new image on the external display surface of the adjustable lens; and displaying, by the wearable computing device, a different image on the external display surface of the adjustable lens in response to a determination to display a new image.

Example 51 includes one or more machine-readable storage media comprising a plurality of instructions stored thereon that, when executed, cause a wearable computing device to perform the method of any of Examples 26-50.

Example 52 includes a wearable computing device to control vision correction, the wearable computing device comprising means for controlling an opacity of an adjustable lens of the wearable computing device to generate a viewing port through the adjustable lens such that a region defined by the viewing port has an opacity less than a remaining region of the adjustable lens; means for receiving eye tracking sensor data from an eye tracking sensor of the wearable computing device; means for determining a gaze direction of an eye of a user of the wearable computing device based on the eye tracking sensor data; and means for adjusting the viewing port based on the gaze direction of the user.

Example 53 includes the subject matter of Example 52, and wherein the means for controlling the opacity of the adjustable lens comprises means for controlling the opacity of the adjustable lens to generate a viewing port based on a prescription received from a remote server.

Example 54 includes the subject matter of any of Examples 52 and 53, and wherein the means for controlling the opacity of the adjustable lens comprises means for determining at least one of an initial location, initial size, or initial shape of the viewing port, and means for controlling the opacity of the adjustable lens to generate a viewing port at the initial location, having the initial size, or having the initial shape.

Example 55 includes the subject matter of any of Examples 52-54, and wherein the means for receiving the eye tracking sensor data comprises means for receiving eye tracking sensor data indicative of a gaze direction of each of two eyes of the user.

Example 56 includes the subject matter of any of Examples 52-55, and wherein the means for adjusting the viewing port comprises means for adjusting the viewing port based on an elapsed time.

Example 57 includes the subject matter of any of Examples 52-56, and wherein the means for adjusting the viewing port comprises means for adjusting at least one of a location, a size, or a shape of the viewing port.

Example 58 includes the subject matter of any of Examples 52-57, and further including means for determining a focus magnitude of the eye the user based on the eye tracking data, wherein the focus magnitude is indicative of an amount of focus exhibited by the eye of the user, and wherein the means for adjusting the viewing port comprises means for adjusting the viewing port based on the gaze direction and focus magnitude of the user.

Example 59 includes the subject matter of any of Examples 52-58, and further including means for generating an image of an external environment of the wearable computing device; and means for determining a viewing context of the user based on the image of the external environment, wherein the means for adjusting the viewing port comprises means for adjusting the viewing port based on the gaze direction of the user and the viewing context of the user.

Example 60 includes the subject matter of any of Examples 52-59, and wherein the means for determining a viewing context of the user comprises means for determining an activity currently being performed by the user.

Example 61 includes the subject matter of any of Examples 52-60, and further including means for generating usage data indicative of the user's usage of the wearable computing device over a period of time.

Example 62 includes the subject matter of any of Examples 52-61, and wherein the means for generating usage data comprises means for generating gaze data indicative of the gaze direction of the eye of the user over the period of time.

Example 63 includes the subject matter of any of Examples 52-62, and wherein the means for generating the usage data comprises means for determining a focus magnitude of the eye the user based on the eye tracking data, wherein the focus magnitude is indicative of an amount of focus exhibited by the eye of the user; and means for generating focus data indicative of the focus magnitude of the eye of the user over the period of time.

Example 64 includes the subject matter of any of Examples 52-63, and further including means for transmitting the usage data to a remote server; and means for receiving, from the remote server, an updated prescription based on the usage data, wherein the means for adjusting the viewing port comprises means for adjusting the viewing port based on the updated prescription.

Example 65 includes the subject matter of any of Examples 52-64, and wherein the means for adjusting the viewing port comprises means for adjusting the viewing port based on the usage data.

Example 66 includes the subject matter of any of Examples 52-65, and further including means for displaying an image on an external display surface of the adjustable lens.

Example 67 includes the subject matter of any of Examples 52-66, and further including means for retrieving the image from a local data storage of the wearable computing device.

Example 68 includes the subject matter of any of Examples 52-67, and further including means for establishing a communication link with a local computing device; and means for receiving the image from the local computing device via the communication link.

Example 69 includes the subject matter of any of Examples 52-68, and wherein the means for displaying the image comprises means for displaying the image for a reference period of time.

Example 70 includes the subject matter of any of Examples 52-69, and further including means for determining whether to display a new image on the external display surface of the adjustable lens; and means for displaying a different image on the external display surface of the adjustable lens in response to a determination to display a new image.

Example 71 includes the subject matter of any of Examples 52-70, and wherein means for displaying the image comprises means for displaying the image on the adjustable lens without the viewing port.

Example 72 includes a wearable computing device to control vision correction, the wearable computing device comprising means for determining an image for display on an external display surface of an adjustable lens of the wearable computing device; and means for displaying the image on the external display surface of the lens of the wearable computing device, wherein the means for displaying the image comprises means for electronically controlling an opacity of the adjustable lens.

Example 73 includes the subject matter of Example 72, and further including means for retrieving the image from a local data storage of the wearable computing device.

Example 74 includes the subject matter of any of Examples 72 and 73, and further including means for establishing a communication link with a local computing device; and means for receiving the image from the local computing device via the communication link.

Example 75 includes the subject matter of any of Examples 72-74, and wherein the means for displaying the image comprises means for displaying the image for a reference period of time.

Example 76 includes the subject matter of any of Examples 72-75, and further including means for determining whether to display a new image on the external display surface of the adjustable lens; and means for displaying a different image on the external display surface of the adjustable lens in response to a determination to display a new image.

The invention claimed is:

1. A wearable computing device to control vision correction, the wearable computing device comprising:
   one or more adjustable lens, wherein each adjustable lens has an opacity that is electronically adjustable;
   one or more eye tracking sensors to generate eye tracking sensor data of an eye of a user;
   an eye tracking module to determine a gaze direction of the eye of the user based on the eye tracking data; and
   a lens control module to (i) control an opacity of an adjustable lens of the one or more adjustable lens to generate a viewing port through the adjustable lens and (ii) adjust the viewing port based on the gaze direction of the eye of the user, wherein a region defined by the viewing port has an opacity less than a remaining region of the adjustable lens.

2. The wearable computing device of claim 1, wherein the lens control module is to control the opacity of the adjustable lens to generate the viewing port based on a prescription received from a remote server.

3. The wearable computing device of claim 1, wherein to adjust the viewing port comprises to adjust at least one of a location, a size, or a shape of the viewing port.

4. The wearable computing device of claim 1, wherein the eye tracking module is further to determine a focus magnitude of the eye of the user based on the eye tracking data, wherein the focus magnitude is indicative of an amount of focus exhibited by the eye of the user, and the lens control module is to adjust the viewing port based on the gaze direction and the focus magnitude of the user.

5. The wearable computing device of claim 1, further comprising:
   a camera to generate an image of an external environment of the wearable computing device; and
   a context determination module to determine a viewing context of the user based on the image of the external environment,
   wherein to adjust the viewing port comprises to adjust the viewing port based on the gaze direction of the user and the viewing context of the user.

6. The wearable computing device of claim 1, wherein the eye tracking module is further to generate usage data indicative of the user's usage of the wearable computing device over a period of time.

7. The wearable computing device of claim 6, wherein to generate the usage data comprises to generate gaze data indicative of the gaze direction of the eye of the user over the period of time.

8. The wearable computing device of claim 6, wherein to generate the usage data comprises to:
   determine, a focus magnitude of the eye the user based on the eye tracking data, wherein the focus magnitude is indicative of an amount of focus exhibited by the eye of the user; and
   generate focus data indicative of the focus magnitude of the eye of the user over the period of time.

9. A wearable computing device to control vision correction, the wearable computing device comprising:
   one or more adjustable lens, wherein each adjustable lens has an opacity that is electronically adjustable and includes an external display surface;
   an image determination module to determine an image for display on the external display surface of an adjustable lens of the one or more adjustable lens; and
   a lens control module to control the opacity of the adjustable lens and display the image on the external display surface of the adjustable lens.

10. The wearable computing device of claim 9, wherein the lens control module is to:
    establish a communication link with a local computing device, and
    receive the image from the local computing device via the communication link.

11. One or more non-transitory machine-readable storage media comprising a plurality of instructions stored thereon that, when executed, cause a wearable computing device to:
    control an opacity of an adjustable lens of the wearable computing device to generate a viewing port through the adjustable lens such that a region defined by the viewing port has an opacity less than a remaining region of the adjustable lens;
    receive eye tracking sensor data from an eye tracking sensor of the wearable computing device;
    determine a gaze direction of an eye of a user of the wearable computing device based on the eye tracking sensor data; and
    adjust the viewing port based on the gaze direction of the user.

12. The one or more non-transitory machine-readable storage media of claim 11, wherein to control the opacity of the adjustable lens comprises to control the opacity of the adjustable lens to generate a viewing port based on a prescription received from a remote server.

13. The one or more non-transitory machine-readable storage media of claim 11, wherein to adjust the viewing port comprises to adjust at least one of a location, a size, or a shape of the viewing port.

14. The one or more non-transitory machine-readable storage media of claim 11, wherein the plurality of instructions further cause the wearable computing device to determine a focus magnitude of the eye the user based on the eye tracking data, wherein the focus magnitude is indicative of an amount of focus exhibited by the eye of the user, and
wherein to adjust the viewing port comprises to adjust the viewing port based on the gaze direction and focus magnitude of the user.

15. The one or more non-transitory machine-readable storage media of claim 11, wherein the plurality of instructions further cause the wearable computing device to:
generate, by a camera of the wearable computing device, an image of an external environment of the wearable computing device; and
determine a viewing context of the user based on the image of the external environment,
wherein to adjust the viewing port comprises to adjust the viewing port based on the gaze direction of the user and the viewing context of the user.

16. The one or more non-transitory machine-readable storage media of claim 11, wherein the plurality of instructions further cause the wearable computing device to generate gaze data indicative of the gaze direction of the eye of the user over the period of time.

17. The one or more non-transitory machine-readable storage media of claim 11, wherein the plurality of instructions further cause the wearable computing device to:
determine a focus magnitude of the eye the user based on the eye tracking data, wherein the focus magnitude is indicative of an amount of focus exhibited by the eye of the user; and
generate focus data indicative of the focus magnitude of the eye of the user over the period of time.

18. The one or more non-transitory machine-readable storage media of claim 11, wherein the plurality of instructions further cause the wearable computing device to display an image on an external display surface of the adjustable lens.

19. A method for controlling vision correction of a wearable computing device, the method comprising:
controlling, by the wearable computing device, an opacity of an adjustable lens of the wearable computing device to generate a viewing port through the adjustable lens such that a region defined by the viewing port has an opacity less than a remaining region of the adjustable lens;
receiving, by the wearable computing device, eye tracking sensor data from an eye tracking sensor of the wearable computing device;
determining, by the wearable computing device, a gaze direction of an eye of a user of the wearable computing device based on the eye tracking sensor data; and
adjusting, by the wearable computing device, the viewing port based on the gaze direction of the user.

20. The method of claim 19, wherein adjusting the viewing port comprises adjusting at least one of a location, a size, or a shape of the viewing port.

21. The method of claim 19, further comprising determining, by the wearable computing device, a focus magnitude of the eye the user based on the eye tracking data, wherein the focus magnitude is indicative of an amount of focus exhibited by the eye of the user, and
wherein adjusting the viewing port comprises adjusting, by the wearable computing device, the viewing port based on the gaze direction and focus magnitude of the user.

22. The method of claim 19, further comprising:
generating, by a camera of the wearable computing device, an image of an external environment of the wearable computing device; and
determining, by the wearable computing device, a viewing context of the user based on the image of the external environment,
wherein adjusting the viewing port comprises adjusting, by the wearable computing device, the viewing port based on the gaze direction of the user and the viewing context of the user.

23. The method of claim 19, further comprising generating, by the wearable computing device, gaze data indicative of the gaze direction of the eye of the user over the period of time.

24. The method of claim 19, further comprising:
determining, by the wearable computing device, a focus magnitude of the eye the user based on the eye tracking data, wherein the focus magnitude is indicative of an amount of focus exhibited by the eye of the user; and
generating, by the wearable computing device, focus data indicative of the focus magnitude of the eye of the user over the period of time.

25. The method of claim 19, further comprising displaying an image on an external display surface of the adjustable lens.

* * * * *